(12) United States Patent
Maurya et al.

(10) Patent No.: US 6,562,791 B1
(45) Date of Patent: May 13, 2003

(54) GLUCOPYRANOSIDE, PROCESS FOR ISOLATION THEREOF, PHARMACEUTICAL COMPOSITION CONTAINING SAME AND USE THEREOF

(75) Inventors: Rakesh Maurya, Jammu (IN); Deepa Singh, Jammu (IN); Asha Bhagat, Jammu (IN); Om Parkash Gupta, Jammu (IN); Sukhdev Swami Handa, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/112,229

(22) Filed: Mar. 29, 2002

(51) Int. Cl.$^7$ ................ A61K 31/7042; A61K 31/7028; A61K 31/70
(52) U.S. Cl. .................... 514/23; 514/866; 514/456; 536/124; 536/128
(58) Field of Search .................. 514/23, 456, 866; 536/124, 128

(56) References Cited

U.S. PATENT DOCUMENTS 5,886,029 A  3/1999 Dhaliwal .................... 514/456

FOREIGN PATENT DOCUMENTS

EP  0 956 867 A1  11/1999

OTHER PUBLICATIONS

Dama Adinarayana et al., *Phytochemistry*, 1982, 21(5):1082–1085.
K.R. Kirtikar et al., *Indian Medicinal Plants*, 1975, 3:2126–2137.
J. Matthew et al., *Current Science*, 1984, 53(11):576–577.
Poonam Mohan et al., *Phytochemistry*, 1989, 28(4):1287–1288.
B.K. Chakravarthy et al., *Planta Medica*, 1985, 1, 56–59.
Prithwi Nath Bhargava, *Proceedings of the Indian Academy of Sciences*, 1947, 24:496–500.
S. Kumar et al., *Ind. J. Physio. and Pharma.*, 1971, 15(2):51.
G.C. Sepaha et al., *J. Ind. Med. Assoc.*, 1956, 27(10):388–391.
Nilima Banerji et al., *J. Inst. Chemists* (India), 1994, 66, 95–96.
Anjali Ghosh et al., *J. Inst. Chemists* (India), 1995, 67, 50–54.
M. Manickam et al., *J. Nat. Prod.*, 1997, 60, 609–610.
PCT Search Report.
S.K. Jain et al., *Medicinal Plants*, 1968, 116–118.
R.N. Chopra et al., *Indigenous Drugs of India*, 1958, 522.
K.R. Kirtikar et al., *Indian Medicinal Plants*, 1980, 2135–2136.
B.K. Chakravarthy et al., *Lancet*, 1983, 272–273.
H. Kolb et al., *Lancet*, 1982, 1303–04.
B.K. Chakravarthy et al., *Lancet*, 1981, 759–60.
J.S. Dunn et al., *Lancet*, 1943, 384–387.
J.S. Dunn et al., *Lancet*, 1943, 484–487.
FDW Lukenes, *Physiol. Rev.*, 1984, 28:304–330.
B.K. Chakravarthy et al., *Life Sci.*, 1981, 29:2043–2047.
B.K. Chakravarthy et al., *Ind. J. Pharmac.*, 1980, 12:123–127.
E.W. Sheehan et al., *J. Natl Prod.*, 1983, 46(2):232–234.
D.S. Shah, *Ind. J. Med. Res.*, 1967, 55(2):166–168.
S.S. Gupta, *Ind. J. Med. Res.*, 1963, 51(4):716–724.
Padmini Kedar et al., *Maharashtra Med. J.*, 1981, 28(6):165–169.
A.V. Subba Rao et al., *Phytochemistry*, 1982, 21(7):1837–1838.
James Matthew et al., *Phytochemistry*, 1983, 22(3):794–795.
A.V. Subba Rao et al., *Phytochemistry*, 1984, 23(4):897–898.
Subhash C. Jain et al., *Phytochemistry*, 1997, 44(4):765–766.
Dama Adinarayana et al., *Zeitschrift Fur Naturforschung*, 1982, 37C:145–147.
J. Mitra et al., Phytochemistry, 1982, 21(9):2429–2430.
J. Mitra et al., *Phytochemistry*, 1983, 22(10):2326–2327.
Rakesh Maurya et al., *Heterocycles*, 1982, 19(11):2103–2107.
Rakesh Maurya et al., *J. Natural Prod.*, 1984, 47(1):179–181.
Barend C.B. Bezuidenhoudt et al., *Phytochemistry*, 1987, 26(2):531–535.
John D. Roberts et al., *J. Amer. Chem. Soc.*, 1970, 92(5):1338–1347.
Yukinobu Ikeya et al., *Chem. Pharm. Bull.*, 1994, 42(11):2305–2308.

*Primary Examiner*—Samuel Barts
*Assistant Examiner*—Michael C. Henry
(74) *Attorney, Agent, or Firm*—Morgan & Finnegan, LLP

(57) ABSTRACT

A novel glucopyranoside, 6-hydroxy-2-p-hydroxybenzylbenzofuran-7-C-β-D-glucopyranoside of the formula 1

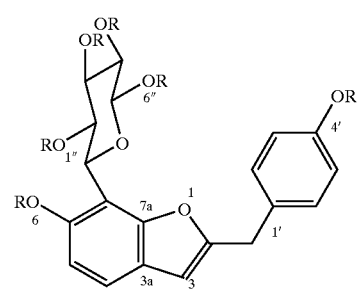

isolated from *Pterocarpus marsupium* and to a process for the isolation thereof is disclosed. The invention also relates to a pharmaceutical composition containing 6-hydroxy-2-p-hydroxybenzylbenzofuran-7-C-β-D-glucopyranoside and to method for the treatment of diabetes using said compound.

13 Claims, No Drawings

GLUCOPYRANOSIDE, PROCESS FOR ISOLATION THEREOF, PHARMACEUTICAL COMPOSITION CONTAINING SAME AND USE THEREOF

FIELD OF THE INVENTION

The present invention relates to a novel glucopyranoside, 6-hydroxy-2-p-hydroxybenzylbenzofuran-7-C-β-D-glucopyranoside of the formula 1

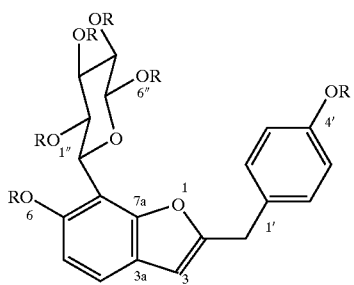

The present invention also relates to a process for the isolation of said novel glucopyranoside of formula 1 from *Pterocarpus marsupium*.

More particularly, the present invention relates to a process of isolation of 6-hydroxy-2-p-hydroxybenzylbenzofuran-7-C-β-D-glucopyranoside of formula 1, from *Pterocarpus marsupium*. The present invention also relates to a pharmaceutical composition containing 6-hydroxy-2-p-hydroxybenzylbenzofuran-7-C-β-D-glucopyranoside of the formula 1 and to method for the treatment of diabetes using said compound of formula 1.

BACKGROUND OF THE INVENTION

*Pterocarpus marsupium* Roxb (Leguminosae) also known as Indian Kino tree or Bijasar, is common in the hilly regions of central and peninsular India [Jain, S. K., Medicinal Plants, National Book Trust, New Delhi, 1968, p. 116]. The extracts of leaves, flowers and gum of this tree have been used medicinally in the treatment of diarrhea, toothache, fever, urinary tract and skin infections. [Chopra, R. N., Chopra, I. C., Handa, K. L. and Kapur, L. D., Indigenous Drugs of India, 2nd Ed., Dhar, U. N. and Sons Private Limited, Calcutta, 1958, p. 522]. The extract of the bark has long been regarded as useful in the therapy of diabetes [Kirtikar, K. R. and Basu, B. D., Indian Medicinal Plants, 2nd Ed., edited by Blatter, E., Cailes, J. F. and Mhaskar, K. S., Singh and Singh, Delhi, India, 1975, V. 2135]. It is reported by Chakravarthy et al [Chakravarthy, B. K., Gupta, S. and Gode, K. D., *Lancet*, 1982, 272 (and references cited therein)] that the active hypoglycemic principle of the bark is (−)-epicatechin and that its effect is due to the regeneration of pancreatic beta cells. However, this claim has been questioned by Kolb et al [Kolb, H., Kiesel, U., Grenlich, B. and Bosch, J. V. D., *Lancet*, 1982, 1303] and Sheehan et al [Sheehan, E. W., Zemaitis, M. A., Slatkin, D. J. and Schiff Jr., P. L., Journal of Natural Products, 1983, 46, 232]. It is now felt that further investigation is necessary before (−)-epicatechin can be considered a viable antidiabetic agent for use in human clinical studies.

Practitioners of the Indian System of Medicine are of the view that the heartwood rather than the bark of *Pterocarpus marsupium* is useful for treatment of diabetic patients and that older the plant more efficacious is its heartwood. It is also claimed that only heartwood that is distinctly red in colour and which imparts a red colouration with bluish green fluorescence to water in which it is kept soaked is suitable for use as an antidiabetic drug.

Hypoglycaemic effects of aqueous or alcoholic extracts of heartwood of *Pterocarpus marsupium* have been verified by experimental [Shah, D. S., *Indian Journal of Medical Research*, 1967, 55, 166 and references cited therein; Gupta, S. S., *Indian Journal of Medical Research*, 1963, 51, 716] and clinical studies [Sepha, G. C. and Bose, S. N., *J. Ind. Med. Assoc.*, 1956, 27, 383; Kedar, P. and Chakrabarti, C. H., *Maharashtra Med. J.*, 1981, 28, 165]. The heartwood of *Pterocarpus marsupium* is rich in phenolics. Chemical investigation on heartwood of *P. marsupium* dates back to 1946 but early works [Bhargava, P. N., *Proc. Ind. Acad. Sci.*, 1946, 24A, 496] on this drug are fragmentary in nature. Previous reported studies on this plant disclose the following chemical constituents.

1. The ether extract of *P. marsupium* heartwood furnished isoflavonoid glycol 4,4-dihydroxy-α-methylhydrobenzoin designated Marsupol [Rao, A. V. S., Mathew, J., *Phytochemistry*, 1982, 21, 1837], a benzofurannone derivative, 2,4',6-trihydroxy-4-methoxybenzo(b)furan-3(2H)-one designated carpusin [Mathew, J. and Rao, A. V. S., *Phytochemistry*, 1983, 22, 794], 2-propanol derivative, 1,3-bis(4-hydroxyphenyl)propan-2-ol, designated propterol [Rao, A. V. S., Mathew, J. and Shankaran, A. V. B., *Phytochemistry*, 1984, 23, 897], 1-(2,4-dihydroxyphenyl)-3-(4-hydroxyphenyl)propan-2-ol designated propterol B [Mathew, J., Rao, A. V. S. and Rambhav, S. *Current Science*, 1984, 53, 576], 6-hydroxy-7-O-methyl-3-(3-hydroxy-4-O-methyl benzyl)chroman-4-one [Jain, S. C., Sharma, S. K., Kumar, R., Rajwansh, V. K. and Babu, V. R., *Phytochemistry*, 1997, 44, 765].

2. Ethyl acetate soluble fraction of alcoholic extract of the heartwood furnished pterosupin β,2',4,4'-tetrahydroxy-3'(c-β-D-glucopyranoside)dihydrochalcone [Adinarayana, D., Syamsundar, K. V., Seligmann, O., and wagner, H., (Z. Naturforsch., 1982, 37C, 145)], Marsupinol [Trivedi, J. J., *Indian J. Phys. Pharmacol*, 1997, 15, 51], 5,4'-dimethoxy-8-methylisoflavone-7-O-α-L-rhamnopyranoside, retusin-O-β-D glucopyranoside and irisolidine-7-O-α-L-rhamnopyranoside [Mitra, J. and Joshi, T., *Phytochemistry*, 1982, 21, 2429] and 5,7'-dihydroxy-6-methoxy-7-O-α-L-rhamnopyranoside [Mitra, J. and Joshi, T., *Phytochemistry*, 1983, 22, 2326] obtained from the ethyl acetate soluble fraction of alcoholic extract of the heartwood.

3. Novel benzofuranone derivative, 2,6-dihydroxy-2-(p-hydroxybenzyl)-4-methoxy-3(2H)-benzofuranone designated marsupin [Maurya, R., Ray, A. B., Duah, F. K., Slatkin, D. J. and Schiff, P. L. Jr., *Heterocycles*, 1982, 19, 2103], pterostilbin, (2S)-hydroxyflavone, isoliquiritigenin, liquiritigenin, 7,4'-dihydroxyflavone, 5-deoxykaempferol and 3,7,4'-trihydroxyflavone [Maurya, R., Ray, A. B. Duah, F. K., Slatkin, D. J. and Schiff, P. L. Jr., *J. Nat. Prod.* 1984, 47, 179], two C-glycosides, 8-C-β-D-glucopyranosyl-3,7,4'-trihydroxy and 3,7,3',4'-tetrahydroxy flavone and 3'-C-β-D-glucopyranosyl-α-hydroxy dihydrochalcone [Bezuidenhoudt, B. C. B., Brandt, E. V., and Ferreira, E. V., *Phytochemistry*, 1987, 26, 531] from ethyl acetate extract of defatted heartwood.

However, the prior art does not provide any details about the biological activities associated with such chemical constituents. Also prior art discloses only preparation of ether extract, ethyl acetate extract and ethyl acetate soluble fraction of the alcoholic extract but does not disclose any method of preparing water extracts of heartwood of *Pterocarpus marsupium* and attempting to isolate any chemical constituents therefrom.

OBJECTS OF THE INVENTION

The main object of the invention is to accordingly prepare water extracts of the heartwood of *Pterocarpus marsupium* and to obtain chemical constituents therefrom.

It is another object of the invention to obtain novel bioactive fractions from water extracts of heartwood of *Pterocarpus marsupium* which are useful in treatment of diabetes.

SUMMARY OF THE INVENTION

The above and other objects of the invention are achieved by partitioning an aqueous extract of powdered heartwood of *Pterocarpus marsupium* with different organic solvents. The novel bioactive fraction, 6-hydroxy-2-p-hydroxybenzylbenzofuran-7-C-β-D-glucopyranoside is isolated from the polar fraction by choromatographic techniques and is found to show hypoglycaemic activity. There is no disclosure in the prior art of this compound since work had been done in the art on the ether extract, ethyl acetate extract and ethyl acetate soluble fraction of the alcoholic extract.

Accordingly, the present invention provides a novel glucopyranoside 6-hydroxy-2-p-hydroxybenzylbenzofuran-7-C-β-D-glucopyranoside of formula 1 where R is H or COCH$_3$

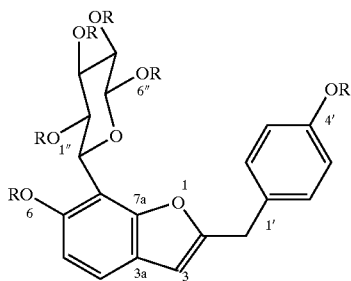

1

The present invention also provides a process for the isolation of 6hydroxy-2-p-hydroxybenzylbenzofuran-7-C-β-D-glucopyranoside of the formula 1 which comprises:
(a) powdering the heartwood of the plant *Pterocarpus marsupium*,
(b) extracting the powdered plant material with a protic solvent,
(c) concentrating the extract to minimum volume and partitioning with different organic solvents of increasing polarity to remove non-polar components, extracting the aqueous layer with polar solvent, removing the solvent to get the residue,
(d) isolating 6-hydroxy-2-p-hydroxybenzylbenzofuran-7-C-β-D-glucopyranoside from the residue.

In one embodiment of the invention, the protic solvent used for preparing the extract in step (b) is selected from the group consisting of water, methanol, ethanol, propanol, butanol and any mixture thereof.

In another embodiment of the invention, the organic solvents used in step (c) comprise solvents of increasing polarity containing 1 to 6 carbon atoms in the molecule.

In another embodiment of the invention, the organic solvents of increasing polarity used in step (c) to remove the nonrpolar components comprise hexane, chloroform, methanol and ethanol in that order.

In another embodiment of the invention the organic solvents of increasing polarity used to extract the aqueous layer comprise hexane, chloroform, ethyl acetate and methanol in that order.

In another embodiment of the invention the organic solvents of increasing polarity used to extract the aqueous layer comprise hexane, chloroform, ethyl acetate, propanol and n-butanol in that order.

In another embodiment of the invention, the chromatographic methods used for the isolation of 6-hydroxy-2-p-hydroxybenzylbenzofuran-7-C-β-D-glucopyranoside is selected from MPLC, HPLC and flash chromatography.

The present invention also provides a pharmaceutical composition containing a pharmaceutically effective amount of 6-hydroxy-2-p-hydroxybenzylbenzofuran-7-C-β-D-glucopyranoside of formula 1 in a pharmaceutically acceptable carrier.

In one embodiment of the invention, the amount of 6-hydroxy-2-p-hydroxybenzylbenzofuran-7-C-β-D-glucopyranoside in said composition is in the range of 0.5 mg to 15 mg per kg of body weight of the patient.

The invention also relates to a method for the treatment of diabetes comprising administering a pharmaceutically effective amount of 6-hydroxy-2-p-hydroxybenzylbenzofiuran-7-C-β-D-glucopyranoside to a patient.

In one embodiment of the invention, the amount of 6-hydroxy-2-p-hydroxybenzylbenzofuran-7-C-β-D-glucopyranoside in said composition is in the range of 0.5 mg to 15 mg per kg of body weight of the patient.

The present invention also relates to the use of 6-hydroxy-2-p-hydroxybenzylbenzofuran-7-C-β-D-glucopyranoside in the preparation of a pharmaceutical composition for the treatment of diabetes.

In one embodiment of the invention, the amount of 6-hydroxy-2-p-hydroxybenzylbenzofuran-7-C-β-D-glucopyranoside in said composition is in the range of 0.5 mg to 15 mg per kg of body weight of the patient.

DETAILED DESCRIPTION OF THE INVENTION

The present invention provides a process for the isolation of 6-hydroxy-2-p-hydroxybenzylbenzofuran-7-C-β-D-glucopyranoside which comprises:
(a) powdering the heartwood of the plant *Pterocarpus marsupium*,
(b) extracting the powdered plant material so prepared with a protic solvent,
(c) concentrating the aqueous extract to minimum volume and partitioning with organic solvents of increasing polarity to remove non-polar components, extracting the aqueous layer with polar solvent, removing the solvent to get the residue;
(d) isolating the 6-hydroxy-2-p-hydroxybenzylbenzofuran-7-C-β-D-glucopyranoside from residue.

The solvent used for preparing the extract may be water, methanol, ethanol, propanol and butanol and like or their mixtures. The organic solvent used in step (c) to remove the non-polar components is selected from hexane, ethyl acetate, methanol, ethanol, propanol, n-butanol and chloroform. The polar solvent used to extract the aqueous layer is selected from ethyl acetate, propanol, butanol and a mixture thereof. The chromatographic methods used for the isolation of methanol, ethanol, propanol may be MPLC, flash chromatography etc.

In the MPLC method the required eluting solvent is pumped through the column and in the flash chromatography solvent is pushed with air pressure. The compound of the invention was recrystallised from a mixture of ethyl acetate and methanol, mp 117–118° C., $[\alpha]_D^{19}$+9.15° (MeOH, c, 0.295), showed UV maxima at 242, 253 and 284 nm in methanol. The molecular formula of the compound was established as $C_{21}H_{22}O_8$ on the basis of strong peak at m/z 402 $[M]^+$ in the FAB mass spectrum, together with the support of spectroscopic methods.

The compound 6-hydroxy-2-p-hydroxybenzylbenzofuran-7-C-β-D-glucopyranoside was isolated from the n-butanol soluble fraction of the water decoction of the heartwood of P. marsupium which has shown antidiabetic activity in both humans and animals. There is no disclosure in the prior art of this compound since work had been done in the art on the ether extract, ethyl acetate extract and ethyl acetate soluble fraction of the alcoholic extract.

The process of isolating active principle from Pterocarpus marsupium comprises partition of the aqueous extract of powdered heartwood with different organic solvents containing 1–6 carbon atoms in the molecule. 6-hydroxy-2-p-hydroxybenzylbenzofuran-7-C-β-D-glucopyranoside of formula 1 is isolated from polar fraction by applying modern chromatographic techniques such as medium pressure liquid chromatography (MPLC), high pressure liquid chromatography (HPLC) and flash chromatography using silica gel (230–400 mesh) and shows hypoglycaemic activity.

The 6-hydroxy-2-p-hydroxybenzylbenzofuran-7-C-β-D-glucopyranoside isolated from Pterocarpus marsupium possesses anti-diabetic activity.

The chromatographic methods used for the isolation of 6-hydroxy-2-p-hydroxybenzylbenzofuran-7-C-β-D-glucopyranoside may be MPLC, flash chromatography etc. In the MPLC method the solvent is pumped through the column and in the flash chromatography is pushed with air pressure. The IR spectrum revealed absorptions at 3300 for hydroxyls, 1600, 1584, 1512 $cm^{-1}$ for aromatic ring. The $^1H$ and $^{13}C$ NMR spectra exhibited two sets of multiplets for aromatic protons centered at δ7.18 (H-5,3',5') and 6.70 (H-4,2',6'), one furan proton singled at δ6.27 (H-3), δC 102.9, a singlet for one benzylic methylene group, at δ3.65, δC 34.2 and multiplet at δ3.00–5.00 for sugar protons. The spectral data suggest that the compound of the invention is a benzofuran C-glucoside containing one phenolic hydroxy group in ring —C. On acetylation the compound of the invention furnished hexa-acetate where in formula 1 R is acetyl, recrystallised from methanol, mp 80–81° C., $[\alpha]_D^{19}$-85.40° ($CHCl_3$, c, 0.185), showed UV maxima at 248, 252; 278, 286 nm in chloroform. IR in KBr 1725, 1600, 1580, 1385 $cm^{-1}$, the molecular formula of the hexaacetate being $C_{33}H_{34}O_{14}$, m/z 655$\{M+1\}^+$. The $^1H$ and $^{13}C$ NMR spectra indicated the presence of four singlets for sugar acetate groups at δ2.17, 2.16, 2.09, and 2.08, two singlets for aromatic acetate groups at δ2.42, and 2.35, one singlet for bynzylic methylene group at δ4.16, δC 34.3, one singlet for furan proton at δ6.38, δC 103.4, two ortho coupled aromatic protons at δ7.46 (1H, d, J=8.4 Hz), and 6.92 (1H, d, J=8.4 Hz), one $A_2B_2$ aromatic system at δ7.36 (2H, d, J=8.3 Hz) and 7.10 (2H, d, J=8.3 Hz). The anomeric proton of sugar appeared at δ5.02 (1H, d, J=9.9 Hz), δC 74.5, indicating it to have the β-configuration on the basis of chemical shift and coupling constant [Roberts J. D., Weigert, F. J., Kroschwitz, J. I. and Reich, H. J., J. Am. Chem.Soc., 1970, 92, 1338]. Further methine protons of sugar appeared at δ5.73 (1H, d, J=9.3 Hz), 5.42 (1H, d, J=9.2 Hz) and 5.28 (1H, d, J=9.4 Hz). Coupling constants for the methine protons H-1" to H-5" of the hexose showed an all trans-axial relationship and together with the methylene (H-6") resonances confirmed the identity of sugar as β-D-glucose. Further the carbon chemical shifts of the glucose moiety were congruent with those of C-β-D-glucopyranosyl residue [Ikeya, Y., Sugama, K., and Maruno, M., Chemistry and Pharmacology Bulletin, 1994, 42, 2305] and HMBC spectra indicated it is linked to aglycone at C-7. On the basis of the above spectral data the structure of the compound was established as 6-hydroxy-2-p-hydroxybenzylbenzofuran-7-C-β-D-glucopyranoside of the formula 1 where R is hydrogen.

The compound was evaluated for hypoglycaemic activity in 18 hour fasted Wistar rats. In a dose of 15 mg/kg p.o., hypoglycaemic effect was recorded in all the treated rats. The mean fall recorded was 24 mg/100 ml blood, from an initial mean of 91 to mean of 67 mg/100 ml blood. As compared to this, conventional hypoglycaemic agents such as chlorpropamide used as a positive control showed mean fall of 18 mg/100 ml of blood.

The invention is described in detail by the examples given below which should not be construed to the limit of scope of the present invention.

EXAMPLE 1

The powdered heartwood of Pterocarpus marsupium (1 kg) was percolated with 80% aqueous ethanol (3×3 lits.) for a period of 48 hours. The resultant concentrate was partitioned with hexane, chloroform, propanol and butanol in that order. The polar extract was subjected to MPLC using silica gel (100–200 mesh) for gross fractions with hexane, chloroform, methanol, ethanol in that order. The active compound was purified by repeated MPLC and flash chromatography over silca gel (230–400 mesh) using $CHCl_3$— MeOH (9:1) as solvent, to furnish 6-hydroxy-2-p-hydroxybenzylbenzofuran-7-C-β-D-glucopyranoside of the formula 1, (yield 0.031–0.041%), mp. 117–118° C., $[\alpha]_D^{19}$+9.15° (MeOH, c, 0.295), and hexaacetate of compound of formula 1 where R is acetyl recrystallised from methanol, mp 80–81° C., $[\alpha]_D^{19}$-85.40° ($CHCl_3$, c, 0.185).

EXAMPLE 2

The heartwood of Pterocarpus marsupium was extracted with hot water for a period of 4 hours. The resultant concentrate was partitioned between hexane, chloroform, propanol and butanol in that order. The polar extract so obtained was subjected to flash chromatography employing silica gel (100–200 mesh) using hexane, chloroform, ethylacetate and methanol as solvent system to afford 6hydroxy-2-p-hydroxybenzylbenzofuran-7-C-β-D-glucopyranoside rich fraction, which on repeated chromatography over silica gel (230–400 mesh) using EtOAc-MeOH (19:1) as solvent, furnished 6-hydroxy-2-p-hydroxybenzylbenzofuran-7-C-β-D-glucopyranoside of the formula 1, (yield 0.032–0.043%), mp. 117–118° C., $[\alpha]_D^{19}$+9.15° (MeOH, c, 0.295), and hexaacetate of compound of formula 1 where R is acetyl recrystallised from methanol, mp 80–81° C., $[\alpha]_D^{19}$-85.40° ($CHCl_3$, c, 0.185).

EXAMPLE 3

The heartwood of Pterocarpus marsupium was boiled with water (16 times) till ¼ volume of water is left, filtered, concentrated and partitioned between hexane, chloroform, ethyl acetate, propanol and n-butanol in that order. The polar extract obtained was subjected to column chromatography employing silica gel (60–120 mesh) using hexane, chloroform, ethyl acetate and methanol as solvent system to afford 6-hydroxy-2-p-hydroxybenzylbenzofuran-7-C-β-D-glucopyranoside rich fraction. The 6hydroxy-2-p-hydroxybenzylbenzofuran-7-C-β-D-glucopyranoside rich fraction on repeated column chromatography over silica gel (100–200 mesh) using mixture of ethyl acetate-acetone (7:3), furnished 6-hydroxy-2-p-hydroxybenzylbenzofuran-7-C-β-D-glucopyranoside of the formula 1 (yield 0.031–0.044%), mp. 117–118° C., $[\alpha]_D^{19}$ +9.15° (MeOH, c, 0.295), hexaacetate of compound of formula 1 where R is acetyl, recrystallised from methanol, mp 80–81° C., $[\alpha]_D^{19}$– 85.40° (CHCl$_3$, c, 0.185).

Advantages:
1. The compound obtained 6-hydroxy-2-p-hydroxybenzylbenzofuran-7-C-β-D-glucopyranoside is a novel molecule with antidiabetic activity.
2 The method of isolation of 6-hydroxy-2-p-hydroxybenzylbenzofuran-7-C-β-D-glucopyranoside is comparatively simple.

We claim:
1. A novel glucopyranoside 6-hydroxy-2-p-hydroxybenzylbenzofuran-7-C-β-D-glucopyranoside of the formula 1

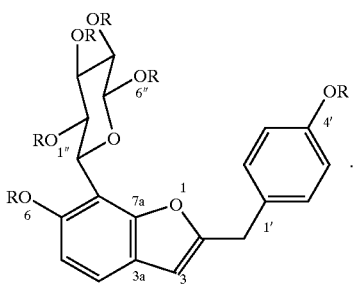

2. Process for the isolation of 6-hydroxy-2-p-hydroxybenzylbenzofuran-7-C-β-D-glucopyranoside of the formula 1

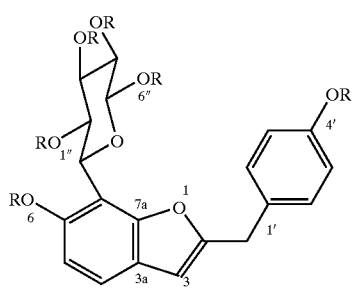

which comprises:
(a) powdering the heartwood of the plant *Pterocarpus marsupium*,
(b) extracting the powdered plant material with a protic solvent,
(c) concentrating the extract to minimum volume and partitioning with different organic solvents of increasing polarity to remove non-polar components, extracting the aqueous layer with polar solvent, removing the solvent to get the residue,
(d) isolating the 6-hydroxy-2-p-hydroxybenzylbenzofuran-7-C-β-D-glucopyranoside from the residue.

3. Process as claimed in claim 2 wherein the protic solvent used for preparing the extract in step (b) is selected from the group consisting of water, methanol, ethanol, propanol, butanol and any mixture thereof.

4. Process as claimed in claim 2 wherein the organic solvents used in step (c) comprise solvents of increasing polarity containing 1 to 6 carbon atoms in the molecule.

5. Process as claimed in claim 2 wherein the organic solvents of increasing polarity used in step (c) to remove the non-polar components comprise hexane, chloroform, methanol and ethanol in that order.

6. Process as claimed in claim 2 wherein the organic solvents of increasing polarity used to extract the aqueous layer comprise hexane, chloroform, ethyl acetate and methanol in that order.

7. Process as claimed in claim 2 wherein the organic solvents of increasing polarity used to extract the aqueous layer comprise hexane, chloroform, ethyl acetate, propanol and n-butanol in that order.

8. Process as claimed in claim 2 wherein the chromatographic methods used for the isolation of 6-hydroxy-2-p-hydroxybenzylbenzofuran-7-C-β-D-glucopyranoside is selected from MPLC, HPLC and flash chromatography.

9. A pharmaceutical composition comprising a pharmaceutically effective amount of 6-hydroxy-2-p-hydroxybenzylbenzofuran-1-C-β-D glucopyranoside.

10. Composition as claimed in claim 9 wherein the amount of 6-hydroxy-2-p-hydroxybenzylbenzofuran-7-C-β-D-glucopyranoside in said composition is in the range of 0.5 mg to 15 mg per kg of body weight of the patient.

11. Method for the treatment of diabetes comprising administering a pharmaceutically effective amount of 6-hydroxy-2-p-hydroxybenzylbenzofuran-7-C-β-D-glucopyranoside to a patient.

12. Method as claimed in claim 11 wherein amount of 6-hydroxy-2-p-hydroxybenzylbenzofuran-7-C-β-D-glucopyranoside in said composition is in the range of 0.5 mg to 15 mg per kg of body weight of the patient.

13. A method of treating diabetes by administering a pharmaceutical composition comprising 6-hydroxy-2-p-hydroxybenzylbenzofuran-1-C-β-D glucopyranoside.

* * * * *